(12) United States Patent
Cussenot et al.

(10) Patent No.: US 9,617,603 B2
(45) Date of Patent: *Apr. 11, 2017

(54) METHOD FOR THE URINARY DETECTION OF BLADDER CANCER

(71) Applicant: ARRAY GENOMICS, Voisins le Bretonneux (FR)

(72) Inventors: Olivier Cussenot, Paris (FR); François Lozach, Chaville (FR); Ian Jones, Voisins le Bretonneux (FR); Neil Metters, Orsay (FR)

(73) Assignee: Array Genomics, Voisins le Bretonneux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,595

(22) Filed: Jun. 4, 2015

(65) Prior Publication Data

US 2015/0322531 A1 Nov. 12, 2015

Related U.S. Application Data

(63) Continuation of application No. 14/569,226, filed on Dec. 12, 2014, now abandoned, which is a
(Continued)

(51) Int. Cl.
| | | |
|---|---|---|
| *C12Q 1/68* | (2006.01) | |
| *C07H 21/02* | (2006.01) | |
| *C07H 21/04* | (2006.01) | |
| *C12P 21/04* | (2006.01) | |
| *G09B 9/56* | (2006.01) | |
| *G01N 33/48* | (2006.01) | |
| *G01N 33/50* | (2006.01) | |

(52) U.S. Cl.
CPC ......... *C12Q 1/6886* (2013.01); *C12Q 1/6837* (2013.01); *C12Q 2600/112* (2013.01); *C12Q 2600/118* (2013.01); *C12Q 2600/158* (2013.01); *C12Q 2600/16* (2013.01)

(58) Field of Classification Search
CPC ............ C12Q 1/6886; C12Q 2600/158; C12Q 1/6837; C12Q 2600/112; C12Q 2600/118; C12Q 2600/16
See application file for complete search history.

(56) References Cited

U.S. PATENT DOCUMENTS

| | | |
|---|---|---|
| 5,965,362 A | 10/1999 | Pinkel et al. |
| 2003/0113758 A1 | 6/2003 | Oudet et al. |

FOREIGN PATENT DOCUMENTS

CA 2 454 866 A1 12/2002

OTHER PUBLICATIONS

Veltman et al., Array-based Comparative Genomic Hybridization for Genome-Wide Screening of DNA Copy Number in Bladder Tumors, Cancer Res. Jun. 1, 2003;63(11):2872-80.*

(Continued)

*Primary Examiner* — Reza Ghafoorian
(74) *Attorney, Agent, or Firm* — RatnerPrestia

(57) ABSTRACT

The invention relates to the diagnosis of bladder cancer and more specifically to the detection in urine samples of bladder carcinomas of the transitional type. The detection method according to the present invention enables, through the utilization of a DNA chip designed for this purpose, to determine the grade of the detected tumors.

17 Claims, 2 Drawing Sheets

Figure 1:
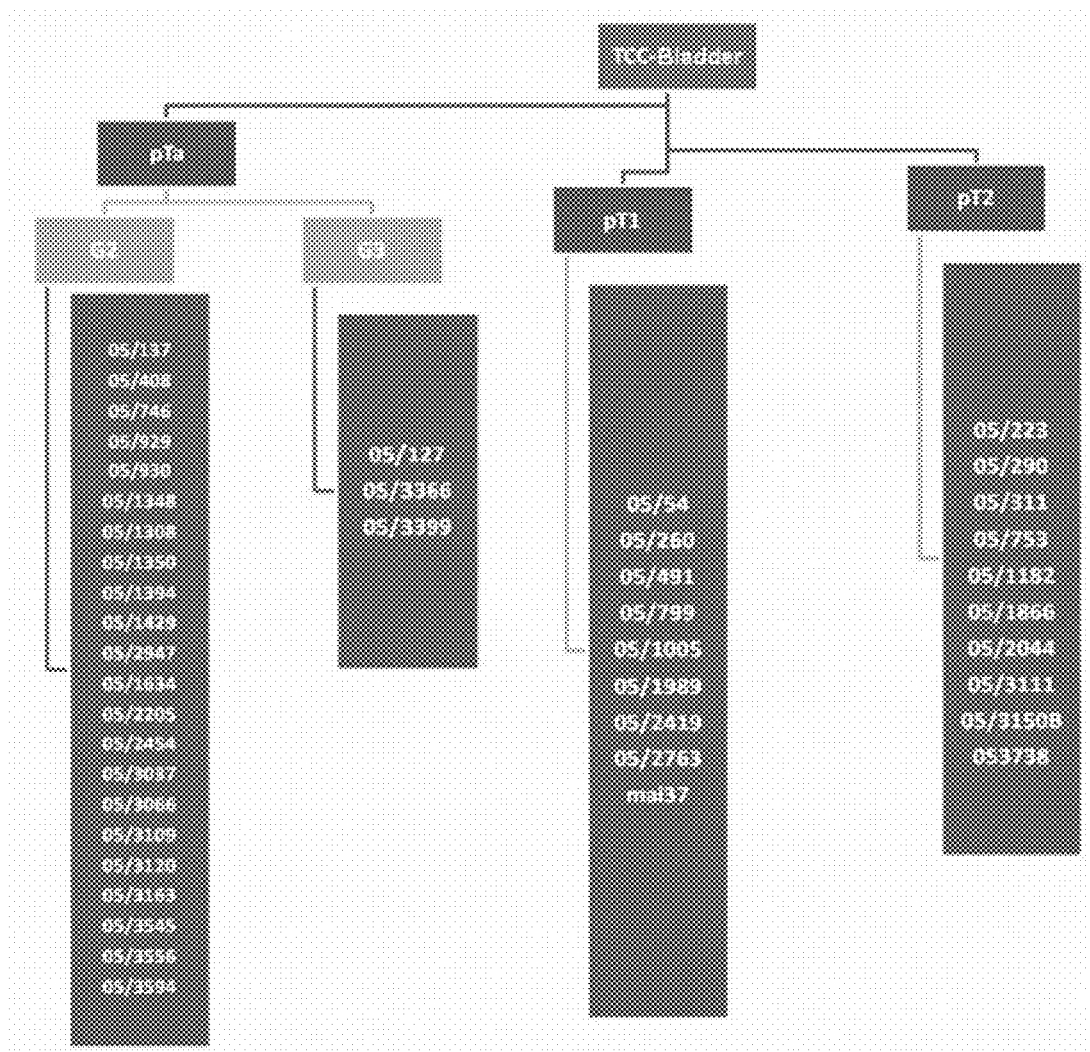

Related U.S. Application Data continuation of application No. 13/107,038, filed on May 13, 2011, now Pat. No. 8,921,070, which is a continuation-in-part of application No. PCT/IB2009/054987, filed on Nov. 10, 2009.

(60) Provisional application No. 61/140,277, filed on Dec. 23, 2008.

(56) References Cited

OTHER PUBLICATIONS

Veltman Joris A. et al.: "Array-based comparative genomics hybridization for genome-wide screening of DNA copy number in bladder." Cancer Research, vol. 63, No. 11, Jun. 1, 2003, pp. 2872-2880, XP002542517.

Snijders A. M. et al.; "Assembly of microarrays for genome-wide measurement of DNA copy number" Nature Genetics, Nature Publishing Group, New Your, NY, US, vol. 29, No. 3, Jan. 1, 2001, pp. 263-264, XP002273931.

Qin S.L. et al.: "Detection of chromosomal alterations in bladder transitional cell carcinomas from Northern China by comparative genomic hybridization" Cancer Letters, New York, NY, US, vol. 238, No. 2, Jul. 18, 2006, pp. 230-239, XP025021859.

Fadl-Elmula Imad et al.; "Chromosomal aberrations in benign and malignant Bilharzia-associated bladder lesions analyzed by comparative genomic hybridization" BMC Cancer, Biomed Central, London, GB, vol. 2, No. 1, Mar. 22, 2002, p. 5, XP021016063.

Leonard Claude et al.; "De la cytogènètique à la cytogènètique des cancers de la vessie" Bulletin Du Cancer (Montrouge), vol. 89, No. 2, 2002, pp. 166-173, XP008110512.

Kallioniemi Anne et al.; "Identification of Gains and Losses of DNA Sequences in Primary Bladder Cancer by Comparative Genomics Hybridization" Genes Chromosomes and Cancer, vol. 12, No. 3, 1995, pp. 213-219, XP002542519.

Mourah Samia et al.: "Assessment of microsatellite instability in urine in the detection of transitional-cell carcinoma of the bladder" International Journal of Cancer, vol. 79, No. 6, Dec. 18, 1998, pp. 629-633, XP002561906.

Garnis C et al.; "OCGR array: an oral cancer genomic regional array for comparative genomic hybridization analysis" Oral Oncology, Elsevier Science, Oxford, GB, vol. 40, No. 5, May 1, 2004, pp. 511-519, XP004495594.

Richter Jan et al.; "Marked Genetic Differences between Stage pTa and Stage pT1 Papillary Bladder Cancer Detected by Comparative Genomic Hybridization" Cancer Research, No. 57, pp. 2860-2864, 1997.

International Search Report dated Jan. 15, 2010 in corresponding Application No. PCT/IB2009/054987, filed Nov. 10, 2009.

Written Opinion of the International Searching Authority in corresponding Application No. PCT/IB2009/054987, filed Nov. 10, 2009.

Blaveri et al., Clin Cancer Res, 11(19):7012-22 (2005).

Richter et al., American Journal of Pathology, 153(5):1615-21 (1998).

Rouprêt et al., Journal Compilation, 101:1448-53 (2008).

\* cited by examiner

METHOD FOR THE URINARY DETECTION OF BLADDER CANCER

CROSS REFERENCE TO RELATED APPLICATIONS

This application is a Continuation application of U.S. patent application Ser. No. 14/569,226, filed Dec. 12, 2014, which is a continuation of U.S. patent application Ser. No. 13/107,038, filed May 13, 2011, which is continuation in part of International Application No. PCT/IB2009/054987, filed Nov. 10, 2009, and claims benefit to U.S. Provisional Application 61/140,277, filed Dec. 23, 2008, all of which are incorporated by reference in its entirety herein.

DESCRIPTION

The invention relates to the diagnosis of bladder cancer and more particularly to the urinary detection of the transitional type of bladder carcinoma (TCC: translational cell carcinoma).

Carcinomas of the transitional type are encountered in transitional epithelium tumors, which comprise approximately 70% to 90% of epithelial bladder tumors. They are characterized by their great morphological variability, so that their prognosis is sometimes difficult to predict.

In terms of histology, urothelial tumors can be papillary or non-papillary, of high or low malignancy (histological grade), infiltrating or non-infiltrating, each lesion being the combined results of these three morphological characteristics.

There are several classifications for urothelial tumors of the bladder. The hitherto most commonly used classification was that of the WHO, which dates back to 1974. It classified transitional cancers of the epithelium as benign (exophytic papilloma, inverted papilloma) or malignant (transitional epithelial carcinomas of grades 1, 2 and 3). In 1998, following several meetings involving anatomic pathologists, urologists, oncologists and biologists, a consensual classification of urothelial tumors was established and validated. It is this new classification (Epstein J. I., *Am. J. Surg. Pathol.* (1998), 22: 1435-1448) which is currently used. Although only slightly different from the previous WHO classification, it has the advantage of being in closer agreement with biology and the evolutive potential of urothelial tumors.

Following this classification, bladder tumors are classified by "grade," from G1 to G3, according to different cytomorphological criteria. The higher the grade, the less differentiated is the cells' appearance and the more aggressive they are.

Tumors are also classified according to their surface characteristics (pTa and T1) or invasiveness in the muscle (from T2 to T4). Low-grade tumors are generally non-invasive or have infiltrated the superficial layers (stages Ta and T1), whereas high-grade tumors are more aggressive and are often detected at T1 or a more advanced stage.

The determination of the grade of the tumor cells has a critical importance for the clinician, as it will help decide which therapeutic methods should be used.

Whereas the presence of invasive grade 3 tumors requires total ablation of the bladder and its accessory glands, most low grade/stage tumors (Ta and T1) can generally be treated locally with the organ remaining intact, by means of different therapeutical approaches such as chemotherapy, immunotherapy or BCG therapy.

Patients affected by a low-grade, non-invasive tumor generally have a good prognosis, but have to be periodically followed up since the risk of cancer relapse is of the order of 70%. Consequently, the patients must be monitored on a regular basis following treatment, every three months for the first two years, and every six months thereafter, and in the case of a relapse it is very important for the tumors' progression to be monitored.

Moreover, low-grade Ta tumors invade the muscle in only 10-15% of cases, whereas T1 tumors progress to grade T2 in 30-35% of cases. High-grade tumors progress more rapidly, with patients quickly reaching grade T2, and remote metastases often forming during the course of the following two years.

Currently, only invasive clinical examinations, in other words involving biopsy, direct endoscopic visualization of the tumors, or surgery can enable a reliable diagnosis to be made of the grade of the tumor cells, and an appropriate therapy to be implemented.

Still, endoscopy is sometimes unreliable and difficult to interpret. As for cytology following a biopsy, various studies show that its reliability is mediocre, resulting in the failed detection of 50% of tumors (Boman, H., et al., 2002, *J. Urol.*, 167(1): 80-83).

On account of the high prevalence of bladder cancer in the population, in particular in persons older than 50, and with the aim to improve both the diagnosis and the comfort of patients, considerable research efforts have been devoted to the development of non-invasive, indirect detection of bladder cancer.

In this respect, several research teams have tried to detect urological tumors by means of urinary samples using conventional tumor marker proteins.

Nevertheless, until now, the detection of these proteins has not been found to be sufficiently specific to be reliable with regard to the origin of the proteins and the stage of development of the tumors.

In 1999, an American team described the possibility of following the progression of bladder cancer by analyzing microsatellite DNA sequences contained in the urine (Steiner et al. (1997) *Nature Medicine* 3: 621-624). This detection method, which consists in amplifying and measuring the variability of some repeated, non coding mitochondrial DNA sequences, is based on the observation that these sequences are generally altered in carcinoma cells.

Nevertheless, this technique is not entirely satisfactory, insofar as it does not effectively enable the grade of the tumors to be determined.

Other molecular methods are based on PCR methods, which attempt to amplify or detect genetic markers, such as local mutations in tumor suppressing genes, applied to the DNAs present in the patients' urine. However, these methods require specific initiators comprising 20 to 40 nucleotides, which are not straightforward to develop, in view of the size and variability of the human genome. In addition, as soon as the DNA of tumor cells is mixed in the urine with the DNAs of healthy cells, the desired amplification is masked by that caused by the latter.

As a result of the difficulty in employing the different known genetic markers of the transitional type of bladder carcinoma, the inventors prefer the use of an innovative approach based on the simultaneous detection of several genetic anomalies frequently encountered in TCC cells.

For this purpose, they listed the main genetic anomalies encountered in transitional bladder carcinomas, then selected those most representative of the grade of the tumor cells. In this approach, they privileged genetic anomalies consisting of physical alterations to the chromosomes, such as ploidies or deletions, typically resulting from the analysis of the karyotype of tumor cells. They then developed an innovative procedure enabling simultaneous detection of the presence or absence of genetic anomalies selected in the DNA contained in the patients' urine.

More particularly, the inventors have selected a specific array of 25 human chromosome loci (using array-based chromosome hybridization comparative analysis techniques with respect to total DNA extracted from a urine sample) providing a significant fluorescent signal.

Until now, tests based on urine samples which offer the same levels of specificity and sensitivity, and which are also able to clearly distinguish between low and high grade tumors have not been made available (Budman L. I. et al., 2008 *CUAJ* 2(3):212-221).

This method has an astonishing ability to diagnose the presence of transitional carcinoma cells of the bladder, with no need for surgical examination of the bladder, whilst providing a good indication of the grade of these tumor cells.

FIG. 1: Classification of the tumors analyzed in the examples, according to the usual clinical criteria.

Figure 2:
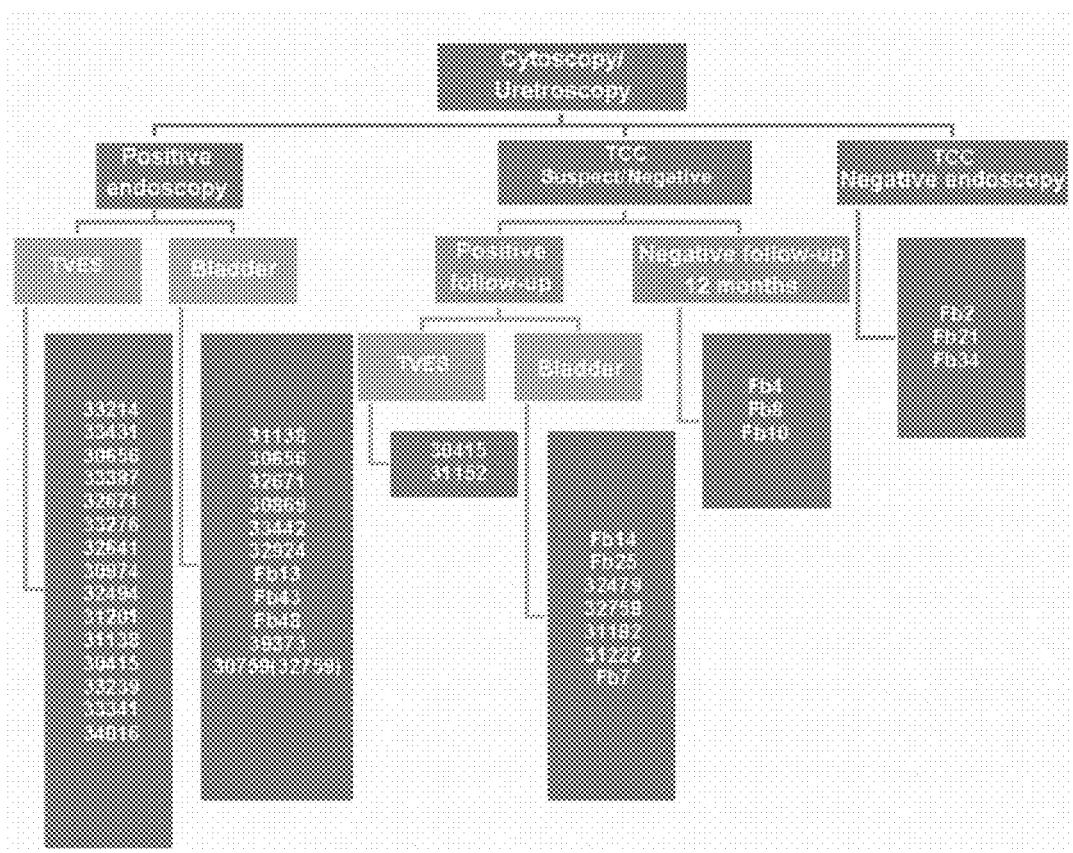

FIG. 2: classification of the patients whose urine was analyzed in the examples, as a function of the results obtained using endoscopy and cytoscopy.

DETAILED DESCRIPTION OF THE INVENTION

The object of the present application is to provide a method for the detection of bladder cancer, more particularly the urinary detection of bladder cancer.

This detection is obtained through the marking of the total quantity of DNA in a patient's urine, and the detection in this DNA, of chromosome sequences comprised in loci, which could potentially be affected by genetic anomalies.

These chromosome sequences, which are the reference DNAs according to the present invention, could potentially be lacking in the case of deletion of the chromosome locus to which they belong, or duplicated, as for example in the case of a trisomy.

Tumor cells in bladder cancer are frequently the source of chromosomal reorganizations, indicative to a certain extent of the tumoral character of the cells. The regions affected by this chromosomal reorganization are however potentially numerous and of variable extent. In effect, although some loci, in particular those which code for tumor suppressing genes or are involved in cell-cycle regulation, are altered more systematically, chromosome anomalies arise when intra and inter-chromosomal recombinations occur between homologous regions, which are not always the same.

According to a first embodiment, one aim of the present invention is to provide a method for the in-vitro detection of bladder cancer in a patient, characterized in that it comprises one or more of the following steps:

In a first step (A), the DNA contained in a urine sample taken from said patient is extracted using one of the numerous methods known to one skilled in the art. As mentioned above, the present invention advantageously allows the cancerous condition of the bladder to be determined based on the patients' urine. This method must therefore concentrate the DNA contained in the urine sample, which DNA is in its residual state since it is derived, in part, from cells present in the bladder. Since the DNA is not a highly fragile material, it is not necessary to take drastic measures in order to preserve the urine samples to be analyzed. The samples can thus be taken at the patients' home. The extracted DNA is complete, in the sense that it contains the entire recoverable DNA present in the urine, whether or not it originates from tumor cells.

In a following step (B), the DNA extracted in step (i) is fragmented, preferably by sonication, into DNA fragments with a size mostly greater than 500 base-pairs (bp), preferably greater than 800 bp, and more preferably between 1000 and 5000 bp. Alternatively, the DNA can be digested by means of enzymes such as restriction enzymes.

In a following step (C), the obtained DNA fragments are marked uniformly, by means of a first marking agent so as to form a pool of marked DNA. Thus, it is the total DNA extracted from the urine which is marked. By "uniformly" it is meant that the marking occurs in a non-specific manner such that two different DNA fragments of identical size are marked with the same intensity. To obtain such marking, one preferably makes use of nucleotides coupled to a fluorophore, which are introduced into the DNA during the course of a replication step. This in-vitro enzymatic replication step can advantageously increase the number of copies of marked DNA fragments available in the DNA pool. The marked DNA pool is comprised preferentially of fragments having random cuts.

In a following step (D), at least one aliquot is formed from the marked DNA pool, said aliquot being capable of forming, according to circumstances, the entire marked DNA pool. Each aliquot is then brought into contact with one, and preferably several, reference DNAs, each of these reference DNAs corresponding to a different DNA sequence included in the locus of a chromosome likely to be affected by a genetic anomaly. Said genetic anomaly is preferably correlated with a specific development stage of bladder cancer and more particularly with a stage such as that mentioned above. The reference DNA can have been chosen, for example, according to data taken from scientific literature or to biopsy analysis results.

According to a preferred embodiment of the present invention, the reference DNAs are comprised of DNA sequences of human chromosomes between 1,000 and 200,000 base pairs (bp) in length, preferably between 2,000 and 180,000 bp in length, and still more preferably between 5,000 and 160,000 bp in length, such as those that are cloned in BAC (Bacterial Artificial Chromosome) or YAC (Yeast Artificial Chromosome) clones constructed from human genome sequences. Such BAC clones are described in the publicly accessible databases relevant to the human genome, such as those of the CNBI or the UCSC.

Thus, whereas it has proven difficult to diagnose bladder cancer based on isolated markers, in particular markers corresponding to short genetic sequences enabling genetic amplification tests to be carried out (PCR, TMA, etc.), the detection method according to the present invention is based on a detection method using DNA sequences which are generally larger than 600 bp.

However, still using hybridization techniques, the present invention may be carried out by using shorter hybridization probes as reference DNAs, more particularly oligonucleotides of 30 to 100 bp in length, preferably of 40 to 80 bp, and more preferably of 50 to 70 base pairs. These shorter probes have given rise to results equivalent as those obtained with the above BAC clones. Even more accurate and sensitive results were obtained by using several different probes from the same chromosome loci or BAC clones. It also provided a more reliable determination of the tumor grade.

According to a preferred embodiment of the invention, the reference DNAs, preferably under the form of previously defined DNA probes, are fixed on a solid substrate, which may take the form of microarray as described further on, micro beads or solid particles. Such solid substrates and their implementation are widely reported in the art.

The inventors have established that it is preferable to use reference DNAs whose sequence are included within the loci of human chromosomes chosen from: 1p, 3q, 8q22qter, 20, 5p12-p13, 9p, 9q, 18q12, 1q22-q24, 5p, 6q22, 7, 11q13, 12q15, 13q, 15, 16, 17q, 6q25-q27, 7q, 8p, 10q, 11p, 14q22-qter, 17p, 19 and 22 as referred to in Table 1. Preferably, the method according to invention involves reference DNAs comprising the DNA sequences included in each of the following loci present in the human chromosomes: 1p, 3q, 8q22qter, 20, 5p12-p13, 9p, 9q, 18q12, 1q22-q24, 5p, 6q22, 7, 11q13, 12q15, 13q, 15, 16, 17q, 6q25-q27, 7q, 8p, 10q, 11p, 14q22-qter, 17p, 19 and 22.

According to the present invention, contact between the marked DNA fragments and the reference DNAs is carried out under conditions enabling specific hybridization, and preferably under stringent conditions such as those described in the experimental part of the present application.

In parallel to step (D), a step (E) consists in preparing a control DNA pool taken from one or several individuals who do not suffer from bladder cancer. Ideally, this DNA is derived from urinary samples taken from several individuals not affected by cancer, chosen randomly from the human population. It is also possible to use commercially prepared, human reference DNA. As in the case of DNA extracted from the patient's urine, the control DNA is uniformly marked by means of a second, preferably fluorescent, marker. This marker is preferably different from that used to mark the patient's DNA.

As in step (D), an aliquot of marked control DNA is brought into contact with the selected reference DNAs, which are identical to those used in step (D). This contacting operation can be carried out separately or jointly, under the same hybridization conditions as those used in step (D). When the contacting operation is carried out jointly, this implies that the patient's DNA and the control DNA are both contacted, preferably simultaneously, with the same reference DNA.

In a following step (F) the marked DNA fragments, which were not specifically hybridized to the reference DNAs in steps (D) and (E), are removed. This step of washing non-hybridized DNAs is carried out according to the procedures known to those in the art, without any particular difficulty.

In a following step (G) the intensity of the signal produced by the marked fragments that have hybridized to each of the selected reference DNAs, are determined. The type and intensity of the signal depends on the type of marker used. When the first and second markers used have equivalent intensities, as for example in the case of cyanines 3 and 5, the variations observed between the patient's DNA and the control DNA are directly related to the quantity of hybridized DNA fragments located at each reference DNA.

In a following step (H), the deviation between the signals recorded from the patient's DNA and from the control DNA is determined for each reference DNA.

According to a preferred embodiment of the present invention, the DNA fragments taken from the patient in step (C) are divided into two pools, with one being marked using a first marker and the second marked using a second marker. The control DNA fragments from step (D) are also divided into two pools, one being marked using the first marker and the second using the second marker. With this procedure, a cross-determination of the signal deviation can be determined with the first and then with the second marker. If the deviations observed between the control DNA and the patient's DNA are of the same order, no matter which marker is used, this is indicative of significant deviations In a following step (I), the cancerous stage of the patient is derived from the deviations observed in the previous step. Thus, according to the present invention, the greater the number of deviations obtained, the more accurate is the detection of bladder cancer. Furthermore, the deviations provide a qualitative indication of the stage of the tumors involved, in particular when several loci indicating the tumoral grade are employed simultaneously.

Alternatively, if a locus is considered to be a highly representative marker of the tumor cells' malignancy, several reference DNAs can be selected from the same locus in order to verify the result derived from this locus.

The method according to the present invention thus enables, in step (I), several reference DNAs to be compared and an extended table of the genetic anomalies encountered to be established. During this step it may then be found useful to weight the results obtained for each reference DNA, in order to take into account, for example, for a tumor at a given stage, the probability of finding a genetic anomaly at the selected locus. When several reference DNAs are used to detect an anomaly on the same locus, it is also possible to weight the deviation obtained for a reference DNA, thereby taking its weight relative to the other represented loci into account. This weighting, or use of constants in order to set correlations between different loci, can be used to design an algorithm enabling a "theoretical stage" to be determined on the basis of data collected during step (H).

The above method can be summarized as a method for in-vitro detection of bladder cancer in a patient, characterized in that it comprises the steps of:

(i) extracting the DNA contained in a urine sample taken from said patient;

(ii) fragmenting the DNA extracted in step (i);

(iii) marking the obtained DNA fragments uniformly with a marking agent so as to form a pool of marked DNA;

(iv) forming at least one aliquot from the pool of marked DNA and bringing each aliquot into contact with a set of reference DNAs, said contact being carried out under conditions enabling specific hybridization of the marked DNA fragments with said reference DNAs;

said reference DNAs comprising the DNA sequences included in each of the following loci present in the human chromosomes: 1p, 3q, 8q22qter, 20, 5p12-p13, 9p, 9q, 18q12, 1q22-q24, 5p, 6q22, 7, 11q13, 12q15, 13q, 15, 16, 17q, 6q25-q27, 7q, 8p, 10q, 11p, 14q22-qter, 17p, 19 and 22;

(v) eliminating the marked DNA fragments which are not specifically hybridized to the reference DNAs;

(vi) determining the intensity of the signal produced by the marked fragments hybridized to each of the selected reference DNAs;

(vii) determining, for each reference DNA, the deviations between the signals obtained in comparison with those obtained with a control DNA from a healthy patient;

(viii) deriving the patient's cancer stage from said observed deviations.

The loci, which are preferably covered by the reference DNAs according to the present invention, are summarized in Table 1.

The reference DNAs correspond to one or several sequences included in the corresponding sequences as referenced by the NCBI (start and end positions on the genome sequence of each chromosome).

TABLE 1

Localization of the reference DNAs

| Chromosomal localization | Start of the genome sequence | End of the genome sequence |
|---|---|---|
| 1p | 20365560 | 113105490 |
| 3q | 123351123 | 182149547 |
| 8q22-qter | 95030146 | 143909236 |
| 20 | 151454 | 57934415 |
| 5p12-p13 | 1771703 | 9682916 |
| 9p | 14010384 | 37091069 |
| 9q | 70785194 | 137897571 |
| 18q12 | 33436616 | 40743026 |
| 1q22-q24 | 154902972 | 158452461 |
| 5p | 1771703 | 9682916 |
| 6q22 | 109464089 | 111511071 |
| 7 | 3863510 | 158689815 |
| 11q13 | 65805698 | 73155080 |
| 12q15 | 55617597 | 78745914 |
| 13q | 25467720 | 99788952 |
| 15 | 25650963 | 97412048 |
| 16 | 267091 | 88643457 |
| 17q | 26415272 | 77690512 |
| 6q25-q27 | 160256061 | 170536116 |
| 7q | 62015315 | 158689815 |
| 8p | 345303 | 38886999 |
| 10q | 42335633 | 135251915 |
| 11p | 399850 | 44925329 |
| 14q22-qter | 72026416 | 106339461 |
| 17p | 7436433 | 21191536 |
| 19 | 9998870 | 54262315 |
| 22 | 20487250 | 48028036 |

The characteristics of the relevant loci can be further defined as follows:

3p: A region having several candidate genes involved in numerous forms of cancer.

4: A region involved more in tumoral progress than in its initiation. Tumor suppressing genes, targeted for other cancerous pathologies, have been described in this region.

5p12-p13: A region involved in tumoral aggressiveness, in particular metastatic spread.

6q: A region involved in high-grade tumors, invading the muscle. The gene M6P/IGF2R is noted as a genetic indicator in the 6q26-q27 locus.

8p: A region frequently deleted in high-grade invasive tumors (especially 8p21-pter) including the tumor suppressing genes: EXTL3, WRN and PRLTS.

9p or entire 9: A region often affected early. The p16/MTS1/CDKN2A/INK4A and p15/MTS2/CDKN2B genes are strong kinase inhibitors in the progression of the cellular cycle. Often affected in the pTas, p16 is an anti-oncogene which depends on Rb, as will be discussed later. INK4A may act on the control points of p53 in particular.

10q or entire 10: A minimal 10q11-q21 and 10q24-q25 region: involved in many other cancers (lymphoma, prostate, colon). This area includes numerous tumor-suppressing genes. 10q deletion could be a factor leading to an incorrect prognosis.

11p: A region corresponding to tumoral aggressiveness, the first threshold in the possible direction of tetraploidy. Deletion could influence the expression of the KAI1 gene (11p11.2), which is a metastasis-suppressing gene. The EXT2, WT1, TSG101 and TSSC5 genes are also involved in other cancers.

13q14: A region corresponding to RB1 in the advanced grades and stages of cancer, RB cooperates with P53. Inactivation of RB facilitates tumoral progression by regulating the initiation of phase S. Other genes could be involved, outside the q14 locus, thus explaining the more extensive deletions generally detected.

14q22-qter: A region which appears to be associated with tumoral progression. Deletion could be caused by unbalanced translocation. At least one tumor-suppressing gene is present at this locus.

16q: A region associated with tumoral progression. CDH1 codes for E cadherin, so that the deletion results in clinical and biological aggressiveness of the tumor cells. Another gene codes for H cadherin, which normally inhibits cellular growth.

17: A deleted or mutated region, which occurs at a later stage, and is associated with tumoral progression rather than initiation. Deletion of p53 at 17p13.1 leads to an increase in the number of genetic alterations due to a lack of control of the P53 protein. The HIC1 gene at 17p13.1 may also be involved.

18q12 or entire 18: A region typically altered in muscle-invading tumors (T2 or more). Smad4/DPC4 and Smad2/MADR2/hMAD2/JU18-1 act on RB and p15 bp inactivating them.

1q22-q25: An amplified region corresponding to the transition between Ta and T1. P73 is often overexpressed, and thus potentially altered by duplication in this area.

3q23-q24-q25-q26-qter: A region already identified as being prone to alteration, even though its involvement has not been proven.

Isochrome 5p (5p gain and associated 5q loss): A region in muscle invading tumors, altered by the activation of proto-oncogenes.

6p22: An amplified region which can be associated with a tumoral invasion due to the possible presence of proto-oncogenes.

7: A region including the ERBB1/EGFR gene at 7p14-p21, coding for an EGF (epidermal growth factor) receptor, which plays a role in cellular growth. At 7q31 the cmet gene codes for another growth receptor, HGF/SF (hepatocyte growth factor/scatter factor). These areas appear to be involved in chaotic cell growth of tumors.

8q: A region often involved in the Ta-T1 transition and the progression towards an invasive and especially metastatic tumor, through the presence of oncogenes in the 8q22-q23 region.

10q22-q23: A region which is rarely amplified, and more commonly deleted (see above).

11: Amplification of at least the 11q13 band with the CCND1 gene which controls entry into the cellular cycle. CCND1 is activated in many cancers but seems to have little correlation with cancer progression. This amplification would entail a relationship with the early cancer growth stages.

12q15: A region containing the MDM2 gene, which interacts with p53 in some tumors in order to suppress its role by masking its activation site.

13q33-q34: Possible trisomy 13, found occasionally in bladder tumors, could lead to duplication of this region possibly containing a proto-oncogene.

17q: A commonly duplicated region including the ERBB2 gene at 17q21. This anomaly is more common in the advanced grades and stages, or associated with relapses.

18q11: A region recognized for some rare significant amplifications.

20: A common region, most often restricted to the 20q locus. Carcinoma proto-oncogenes of the familial form are present at the 20q11-q12 locus. At 20q13, STKIS/BTAK codes for a protein which induces chromosome instability.

According to a preferred aspect of the invention, the in-vitro bladder cancer detection method involves testing for ploidy of the DNA of the patient's urinary cells based on one, several, or all of the following loci: 1q22-q24, 5p, 6q22, 7, 11q13, 12q15, 13q, 15, 16, 17q, 6q25-q27, 7q, 8p, 9p, 9q, 10q, 11p, 14q22-qter, 17p, 18q12, 19 and 22.

According to an alternative embodiment of the present invention, said method involves the testing of DNA ploidy in the patient's urinary cells for one or several of the following loci:

1p, 3q, 8q22qter, 20, 5p12-p13, 9p, 9q, 18q12 and 17p;

1p, 3q, 8q22qter, 20, 5p12-p13, 9p, 9q, 18q12, 17p and 11p;

1p, 3q, 8q22qter, 20, 5p12-p13, 9p, 9q, 18q12, 17p, 11p and 7q;

1p, 3q, 8q22qter, 20, 5p12-p13, 9p, 9q, 18812, 17p, 11p, 7q and 1q22-24;

1p, 3q, 8q22qter, 20, 5p12-p13, 9p, 9q, 18812, 17p, 11p, 7q, 1q22-24 and 11q13;

1p, 3q, 8q22qter, 20, 5p12-p13, 9p, 9q, 18q12, 17p, 11p, 7q, 1 q22-24, 11813 and 8p;

1p, 3q, 8q22qter, 20, 5p12-p13, 9p, 9q, 18q12, 17p, 11p, 7q, 1q22-24, 11q13, 8p and 14q22;

1p, 3q, 8q22qter, 20, 5p12-p13, 9p, 9q, 18q12, 17p, 11p, 7q, 1q22-24, 11813, 8p, 14q22 and 22;

1p, 3q, 8q22qter, 20, 5p12-p13, 9p, 9q, 18q12, 17p, 11p, 7q, 1q22-24, 11q13, 8p, 14q22, 22 and 5p;

1p, 3q, 8q22qter, 20, 5p12-p13, 9p, 9q, 18q12, 17p, 11p, 7q, 1q22-24, 11q13, 8p, 14822, 22, 5p and 6q22;

1p, 3q, 8q22qter, 20, 5p12-p13, 9p, 9q, 18q12, 17p, 11p, 7q, 1q22-24, 11q13, 8p, 14q22, 22, 5p, 6q22 and 7;

1p, 3q, 8q22qter, 20, 5p12-p13, 9p, 9q, 18q12, 17p, 11p, 7q, 1q22-24, 11q13, 8p, 14q22, 22, 5p, 6q22, 7 and 12q15;

1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15 and 15;

1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15, 15 and 6q25-q27;

1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15, 15, 6q25-q27 and 19;

1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15, 15, 6q25-q27, 19 and 13q;

1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15, 15, 6q25-q27, 19, 13q and 16; and 1p, 3q, 8q22qter, 20, 5p12-p13, 9p, 9q, 18q12, 17p, 11p, 7q, 1q22-24, 11q13, 8p, 14q22, 22, 5p, 6q22, 7, 12q15, 15, 6q25-q27, 19, 13q, 16 and 17q.

A further aspect of the present invention involves the use of one or more reference DNAs taken from the 25 loci indicated above in order to determine the grade and aggressiveness of a tumor.

Preferably, the number of different reference DNAs useful for the implementation of the method lies between 2 and 500, preferably between 10 and 400, and still more preferably between 50 and 400.

When using reference DNAs under the form of probes, which are generally of 30 to 100 pb in length, as previously defined, the number of the different probes deposited on the solid support can be much higher, generally from 500 to 100 000, more generally from 1000 to 60 000 probes.

In this respect, the present invention also relates to a DNA microarray or chip, useful for the detection of bladder cancer, more particularly for the urinary detection of this cancer, characterized in that it comprises on its surface several reference DNA deposits, distinct from one another, each of these deposits corresponding to a sequence included in one or more of the loci described above. This DNA microarray or chip, which, preferably, is a glass slide, allows the method according to the present invention to be implemented over a reduced surface area thus enabling simultaneous comparison of the haploid or polyploid state of the patients DNA in the normal diploid state of a healthy DNA for one, several or all of the above mentioned loci. Such a DNA microarray for the detection of bladder cancer according to the invention is preferably characterized in that it comprises on its surface between 10 and 1000 reference DNA deposits, said reference DNAs comprising sequences included in every of the above loci of human chromosomes: 1p, 3q, 8q22qter, 20, 5p12-p13, 9p, 9q, 18q12, 1q22-q24, 5p, 6q22, 7, 11q13, 12q15, 13q, 15, 16, 17q, 6q25-q27, 7q, 8p, 10q, 11p, 14q22-qter, 17p, 19 and 22. Preferentially, each reference DNA deposit comprises a sequence included in the above loci of the human chromosomes.

In accordance with the method previously described, the DNA microarray according to the invention ideally comprises between 10 and 1000, preferably between 10 and 400 DNA, and more preferably between 300 and 400 reference DNA deposits as defined above on its surface. The number of the deposits is reduced in comparison to genomic microarrays for genome wide analysis to diminish background noise. This number is deemed optimal by the inventors to improve the test sensibility with respect to the detection of bladder cancer, using the BAC clones.

Microarrays involving DNA probes are described in the literature [André, F. et al. (2009) Molecular characterization of breast cancer with high resolution oligonucleotide comparative genomic hybridization array, Clin. Cancer. Res. 15(2):441-451]. The specific microarrays according to the invention, which are designed to carry out the detection of bladder cancer from urine samples, comprise the probes selected in the chromosome loci as previously detailed.

By DNA chip is meant a flat glass, silicon or plastic substrate, on which known nucleic DNA sequences, such as the reference DNAs according to the present invention, are placed.

Preferably, according to the present invention, the reference DNA placed on the DNA chip comprises the DNA sequences included only at the loci on which the chromosomal anomalies related to bladder cancer have been described, and preferably at one, several or all of the loci described in the present application.

The present invention also relates to a kit containing one or more of the following elements:

one or more reference DNAs according to the present invention as described in the foregoing, attached to a glass substrate, preferably in the form of a DNA chip or microarray;

a DNA control sample taken from a healthy patient;

a total DNA marker reagent as described in the foregoing; and a software program enabling the comparison between the diploid state of the patient's DNA and the normal diploid state of a control DNA to be analyzed.

Such a kit is preferably packed into a box such as to accommodate all of the tubes, flasks and reagents needed to implement the method according to the present invention.

Further features and advantages of the invention are provided in the following non-limiting examples:

EXAMPLES

A—BAC Clones Microarray Preparation and Analysis

I—Preparation of the Glass Slide

Thanks to the availability of public databases (UCSC and NCBI), a series of BAC clones (DNA portions from the human genome) were selected to cover the chosen markers listed in Table 1. The position of these clones was confirmed by sequencing the two ends of the cloned DNA in order to verify the exact position of the DNA sequence in the genome. Each of these clones forms a reference DNA as implied by the present invention.

The totality of selected clones covers all of the chromosomal loci chosen as markers, making a total of 341 BAC clones.

The DNA was extracted from the BAC and amplified using repliG technology (Qiagen, Germany). Each DNA was placed so as to form 341 wells in a PCR plate, each containing 10 µg of purified DNA. By means of a Biorobotic robot and 4 needles, the DNA was placed in very small quantities onto a glass slide. The design, produced by ArrayGenomics, incorporates two hybridization areas enabling, as a precaution, a twin experiment to be carried out. Each DNA is randomly placed 5 times in each hybridization area in order to obtain 5 Independent measurements.

The DNA was then chemically fixed onto a glass slide enabling it to be preserved for 3 to 6 months.

II—Genetic Profile of Bladder Tumors

Frozen tumors were collected. The chromosomal DNA of these tumors is extracted using a commercial kit. The tumors considered to be of a "low grade" are at stage pTa/G2, The tumors considered to be of a "high grade" are at least at stage pTa/G3, pT1 and pT2. The tumors are classified according to the standard clinical criteria (FIG. 2).

The DNA extracted from the frozen tumors is quantified by fluorometry (QuBit system, Invitrogen).

The human genomic DNA used as a control sample for the implementation of the diagnostic method is commercial DNA (promega, human genomics DNA).

III—DNA Marking and Hybridization with the Reference DNAs Marking of the Entire DNAs 1. 2.3 µg of control DNA is fragmented by sonication in a 55 µl eppendorf tube using a sonicator (Elmasonic sonicator) for 12 to 13 seconds.
2. 200-300 ng of DNA prepared by this means are checked by electrophoresis on an 0.8% agarose gel, in order to verify that the DNA is correctly fragmented and that most of the fragments has a size greater than 600 bp.
3. The fragments are purified in micro-columns (NucleospinExtract II).
4. 25 µl (~1 µg) aliquots of purified DNA and control DNA are placed in centrifuging tubes for marking with Cy5 and Cy3 fluorophores.
5. 20 µl of random sequence primers (tube 1, Enzo Kit) are added to each tube, then vortexed and centrifuged.
6. The tubes are warmed in a water bath at 99° C. for 10 minutes.
7. The tubes are placed in ice for 5 minutes then briefly centrifuged and returned to the ice.
8. 5 µl of a mixture of nucleotides marked with cyanin are added to each tube (tube 2 or 3, Enzo Kit).
9. 1 µl of Klenow enzyme fragments (Tube 4, Enzo Kit) is further added.
10. The mixture is incubated in a heat-block for 3 hours and 30 minutes at 37° C.
11. 5 µl of Stop Buffer (tube 5, Enzo Kit) is added following which the tubes are placed onto Ice.

Washing of the Marked DNA 12. 200 µl of NT buffer per 100 µl of DNA are added to the tubes.
13. The contents of each tube are transferred to a column, and then centrifuged for 1 minute at 11,000 g.
14. 600 µl of a NT3 washing buffer is placed in each column, and then centrifuged for 1 minute at 11,000 g.
15. The columns are centrifuged for 2 minutes at 11,000 g.
16. 51 µl of sterile water is placed at the top of the column for 1 minute.
17. The column is centrifuged for 1 minute at 11,000 g and the dissolved marked DNA is recovered in a tube.

Preparation of the DNA Before Hybridization 18. 50 µl of Cot-1 DNA (Roche) was added to each tube.
19. The volume is adjusted to 200 µl using 0.3M of sodium acetate (pH 5-8).
20. 300 µl of frozen ethanol was added.
21. The mixture is vortexed and then incubated in darkness at 70° C. for 15 minutes.
22. The tubes are centrifuged for 15 minutes at 11,000 g between 4 and 8° C.
23. The supernatant is removed using a vacuum pump.

Preparation of the BAC on a Glass Slide

The DNAs in the form of BAC clones are placed in dehydrated form on a glass plate then fixed using a cross-linkage agent sensitive to UV light (350 mJ).

Hybridization of Marked DNA/Reference DNA (BAC)

24. The residue recovered in point 23 is added to 5 µl of ddH2O.
25. 10 µl for 50 µg/µl of tRNA yeast (Invitrogen, Cat #15401-011) and the mixture is stirred and warmed to 95° C. for 5 minutes.
26. 15 µl of hybridization buffer (Ambion Slide Hyb Buffer #3) preheated to 70° C. is added.
27. The mixture is stirred vigorously for 30 seconds and centrifuged at 13,000 rpm for 30 seconds.
28. The mixture is warmed to 37° C. for 30 minutes.
29. The glass slide is entirely covered by the mixture.
30. A clean Lifterslip leaf (24×32 inches) (Erie Scientific, Cat #25X60I-2-4789) is placed above the glass slide in order to cover the microarray.
31. 20 µl of water was added in order to humidify the seals.
32. The closed hybridization chamber (Hybridization chamber, Corning, Cat #2551) is immersed in a water bath at 55° C. for 16 hours.

Post-Hybridization Washing

33. The glass plate is incubated in a first solution of 0.1% SDS 0.1×SSC, at 50° C.

The microarray is then placed successively in the following washing solutions (in each solution, for 45 sec while stirring and for 45 sec without stirring):

a) 0.1×SSC, 0.1% SDS;
b) 0.1×SSC, 0.1% SDS;
c) 0.1×SSC;
d) 0.1×SSC;

34. The glass slide is immersed at room temperature in a marking box filled with a 0.1×SSC solution then in another box filled with 100% ethanol (CML, Cat# BVITRI-PPL25L).
35. The glass slides are then placed in conical 50 ml tubes and then centrifuged for several seconds to dryness.

36. The glass slides are preserved in darkness.

The glass slides are analyzed using a fluorescent scanner (GENEPIX 4000B) with a sensitivity adjusted according to the intensity of the marking signal.

The results are analyzed using the image analysis software BacMagic$_+$ (developed by ARRAYGENOMICS) to graphically visualize the profiles in the dye swap mode. For each DNA, a text file is exported by BacMagic$_+$ and formatted so that it can be used by the seeGH software. Deletions and gains are annotated based on visualization of the dye swap symmetry in BacMagic$_+$.

Using seeGH, for each group, the annotations are compiled in order to derive an overall image of the detected anomalies and their frequency. In these figures, which are similar to a karyotype table, the marks represent anomalies (red=loss, green=gain) and their location. The sizes of the marks represent their detection frequency in the patient pool.

Analyzing FIG. 2 it is possible to create a typical profile of each tumor group according to its grade and stage, which can then be compared to typical profiles of tumor groups.

TABLE 2

Gains visualized after analysis of the detected anomalies

| BANDS | TOTAL CLONES | POSITIVE MINIMUM | pTa G2 | pTa G3 | T1 | T2 |
|---|---|---|---|---|---|---|
| 1q22-24 | 4 | 3 | | 2 | 2 | |
| 3q | 6 | 5 | 2 | 1 | | |
| 5p | 7 | 6 | 2 | | | |
| 8q22-ter | 3 | 2 | 1 | 2 | 2 | 1 |
| 11q13 | 7 | 6 | | 2 | | |
| 12q21-24 | 5 | 4 | | | 1 | |
| 15 | 8 | 6 | | | 1 | |
| 16 | 12 | 10 | | | 1 | 2 |
| 17q | 11 | 9 | | | 1 | |
| 18q | 10 | 8 | | | | 2 |
| 20q11-ter | 10 | 8 | | 1 | | |
| 20 | 14 | 11 | 1 | | 2 | 1 |

TABLE 3

Deletions visualized after analysis of the detected anomalies

| BANDS | TOTAL CLONES | POSITIVE MINIMUM | pTa G2 | pTa G3 | T1 | T2 |
|---|---|---|---|---|---|---|
| 2q35-ter | 2 | 2 | | | 1 | |
| 4q26-ter | 7 | 6 | | | 1 | |
| 6q25-27 | 5 | 4 | | 1 | 4 | 3 |
| 8p | 14 | 11 | | 2 | 2 | 2 |
| 9p | 6 | 5 | 1 | 1 | | |
| 9q | 12 | 10 | 3 | 2 | 2 | 1 |
| 10q | 14 | 11 | | 1 | | |
| 11p | 4 | 3 | | 1 | 3 | |
| 11q23-25 | 5 | 4 | | 1 | 1 | 1 |
| 13q13 | 3 | 2 | | | 2 | 1 |
| 13 | 7 | 6 | | 1 | 1 | 2 |
| 14q23-31 | 3 | 2 | | | | 2 |
| 17p | 5 | 4 | | | 1 | |
| 17 | 16 | 13 | | | 1 | 1 |
| 18q12 | 3 | 2 | 1 | 1 | | |
| 18q12-23 | 11 | 9 | | | 4 | |
| 19 | 4 | 3 | | | 1 | 1 |

From this summary, it appears that the pTaG2's are much less altered than the higher grades. Some anomalies seem to be characteristic of low-grade tumors. As described in the literature, deletion 9 is also found here, appearing to be more closely related to initiation and often associated with pTas. In the present case, the 3q and 5p gains also seem to be characteristic of the low grades (here, it is not an iso5p as described for higher grades, since there is no 5q gain).

The gain anomalies for the high grades appear gradually: 8q, 1q, 11q but also 16 and 18, which seem to occur more often in the T2 stages or above.

The loss anomalies for the high grades are 6q, 11p, and 13, but also 18q, the latter event therefore appearing to occur belatedly in the tumor's progression.

IV—Calculation and Definition of Sensitivity and Specificity

Sensitivity: Ability to Detect Sick Patients.

$$\frac{\text{true positive}}{\text{true positive} + \text{false negative}}$$

Specificity: Ability of the Test to Determine which Subjects are Healthy.

$$\frac{\text{true negative}}{\text{true negative} + \text{false positive}}$$

Thanks to the use of known tumors by the inventors, it is possible to compute the test's sensitivity. This will allow the capability of the present technique to detect both low-grade and high-grade tumors to be evaluated. Both groups will be separated in the calculations, because low-grade tumors are less difficult to detect. Routine tests, such as urinary cytology, detect only 50% of these cancers in their initial phase.

The existing tests are characterized by their sensitivity and specificity as computed in the scientific literature (expressed by a minimum and a maximum since these values vary according to each study—Sources: Biomarkers for detection and surveillance of bladder cancer, Lorne I. Budman, MSc, Wassim Kassouf, M. D., and Jordan R. Steinberg, MD from the Division of Urology, McGill University Health Centre, Montreal, Quebec), as indicated in Table 4 below.

TABLE 4

Sensitivity and specificity for the existing tests:

| Test | Sensitivity | Specificity |
|---|---|---|
| BTA Stat (Polymedco) | 52.5%-78.0% | 69.0%-87.1% |
| BTA Trak (Polymedco) | 51%-100% | 73%-92.5% |
| Cytology | 12.1%-84.6% | 78.0%-100% |
| Hematuria dipstick | 47.0%-92.6% | 51.0%-84.0% |
| NMP22 Bladder Cancer Test (Matritech) | 34.6%-100% | 60.0%-95.0% |
| NMP22 BladderChek (Matritech) | 49.5%-65.0% | 40.0%-89.8% |
| ImmunoCyt/uCyt+ (DiagnoCure) | 63.3%-84.9% | 62.0%-78.1% |
| ImmunoCyt/uCyt+ and cytology | 81.0%-89.3% | 61.0%-77.7% |
| UroVysion (Abbott Molecular) | 68.6%-100% | 65.0%-96.0% |

Sensitivity is determined for a given number of markers. For each one of these, a sensitivity value can be computed. Obviously, it is not possible for only one genetic marker to lead to a reliable solution. However, the combination of 25 markers seems to be considerably more judicious, as shown by the summary assessments in Tables 5 and 6.

TABLE 5

Summary assessment based on the 25 markers

| | Gains | | | | Losses | |
|---|---|---|---|---|---|---|
| Locus | Number of abnormal tumors | % | Low Grade | Locus | Number of abnormal tumors | % |
| 1p | 1 | 10% | | 5p12p13 | 1 | 10% |
| 3q | 2 | 20% | | 9p | 3 | 30% |
| 8q22-qter | 4 | 20% | Total sensitivity 80% | 9q | 1 | 10% |
| 11q13 | 4 | 29% | | 18q12 | 2 | 20% |
| 19 | 2 | 14% | | | | |
| 20 | 2 | 20% | | | | |

TABLEAU 6

Summary assessment based on the 25 markers

| | Gains | | | | Losses | |
|---|---|---|---|---|---|---|
| Locus | Number of abnormal tumors | % | High Grade | Locus | Number of abnormal tumors | % |
| 1q22-24 | 4 | 29% | | 6q25-27 | 2 | 14% |
| 3q | 3 | 21% | | 7q | 4 | 29% |
| 5p | 2 | 14% | Total sensitivity 86% | 8p | 3 | 21% |
| 6q22 | 1 | 14% | | 9p | 1 | 7% |
| 7 | 2 | 14% | | 9q | 3 | 21% |
| 8q22qter | 3 | 21% | | 10q | 1 | 7% |
| 12q15 | 1 | 14% | | 11p | 5 | 36% |
| 13q | 2 | 7% | | 13q | 4 | 29% |
| 15 | 2 | 14% | | 14q22qter | 3 | 21% |
| 16 | 1 | 7% | | 16 | 1 | 7% |
| 17q | 1 | 7% | | 17p | 5 | 36% |
| 20 | 1 | 7% | | 18q12 | 4 | 29% |
| 22 | 3 | 21% | | | | |

Specificity: 6 negative DNAs (DNAs without anomalies): 6/(6 + 0)) * 100 = 100%

The 10 anomalies which have been classified in the low-grade group may be taken as models for tumors in their initiation phase, which have not yet become invasive.

Generally, when the tumor is not invasive but of a high grade, or when it is already in the T1 or T2 stage or above, the number of anomalies detected on the markers of this invention increases.

For the high grades, the method does confirm the importance of chromosomes 1, 7, 8, 11, 13, 14, 17, and 18.

However, it should be noted that the sensitivity of each of the markers considered separately does not exceed 36% (as is the case for cytology or NMP22 in some studies).

On the other hand, the pooling of all genetic markers selected by the inventors for the present invention provides very good sensitivity, even for strictly low grades (the result obtained with the present invention ALONE is as satisfactory as the ImmunoCyt/uCyt$_+$ and cytology combination used in certain studies).

Similarly, the specificity (computed for normal samples or for DNAs extracted from the urine of patients with negative endoscopy and negative follow-up results) reaches 100%.

V—Verification on Urine

Urine samples were taken from patients under diagnosis or being followed-up.

Routine endoscopy was performed. The patients were then grouped as shown in FIG. 2.

The method was implemented in the same manner as for the frozen tumors (see part II).

The results are analyzed using the BacMagic$_+$ software to graphically visualize the profiles in the dye swap mode. For each DNA, a text file is exported by BacMagic$_+$ and formatted so that it can be used by the seeGH software. Deletions and gains are annotated based on visualization of the dye swap symmetry in BacMagic$_+$.

Using seeGH, for each group, the annotations are compiled in order to derive an overall image of the detected anomalies and their frequency. In these figures, which are similar to a karyotype table, the marks represent anomalies (red=loss, green=gain) and their location. The sizes of the marks represent their detection frequency in the patient pool.

For tumors of the higher urinary system, it is possible to derive a summary assessment of the detected anomalies (Tables 7 and 8).

TABLE 7

Summary assessment of the detected anomalies (gains)

| BANDS | TOTAL CLONES | POSITIVE MINIMUM | Positive endo | Suspect endo |
|---|---|---|---|---|
| 1q | 10 | 8 | 1 | |
| 1q22-24 | 3 | 2 | | 1 |
| 3 | 19 | | | 1 |
| 3q | 6 | 5 | 1 | |
| 3q26-ter | 3 | 2 | 1 | |
| 5p | 7 | 6 | 1 | 1 |
| 7p | 7 | 6 | | 1 |
| 8q21-23 | 11 | 9 | 2 | 1 |
| 11q13 | 7 | 6 | 1 | |
| 12 | 15 | 12 | 1 | 1 |
| 12q | 7 | 6 | 1 | |
| 13q | 7 | 5.6 | 1 | 1 |
| 15 | 8 | 6.4 | 1 | |
| 16q | 5 | 4 | 1 | 1 |
| 17p | 5 | 4 | | 1 |
| 17q | 10 | 8 | 4 | 1 |
| 19 | 4 | 3 | 4 | 1 |
| 20 | 17 | 14 | 1 | 1 |

TABLE 8

Summary assessment of the detected anomalies (deletions)

| BANDS | TOTAL CLONES | POSITIVE MINIMUM | Positive endo | Suspect endo |
|---|---|---|---|---|
| 1p21-22 | 4 | 3 | 1 | |
| 4q12-13 | 6 | 5 | 1 | |
| 6q25-27 | 3 | 2 | 2 | 1 |
| 8p | 14 | 11 | 2 | 1 |
| 9p | 6 | 5 | 5 | 1 |
| 9q | 12 | 10 | 4 | 1 |
| 10q22 | 3 | 2 | 1 | |
| 11p | 10 | 8 | 1 | 1 |
| 14q23-31 | 4 | 3 | 1 | |
| 17p | 5 | 4 | 1 | 1 |
| 17q | 10 | 8 | 1 | |
| 18q12 | 3 | 2 | | 1 |
| 18q12-23 | 11 | 9 | 5 | |
| 20q | 10 | 8 | 1 | |
| 22q | 8 | 6 | 1 | |

For patients with positive endoscopy, the anomalies characteristic of bladder cancers are recognized, with some variations which are listed here.

Moreover, the anomaly distribution table will be used in an endeavor to determine the grade of these detected tumors.

For bladder tumors, this is also carried out by deriving a summary assessment of the detected alterations.

TABLE 9

Summary assessment of the detected anomalies (gains)

| BANDS | TOTAL CLONES | POSITIVE MINIMUM | Positive endo | Suspect positive endo (follow-up) |
|---|---|---|---|---|
| 1q22-24 | 4 | 2 | 1 | |
| 3p24-ter | 4 | 3 | | 1 |
| 3q | 6 | 5 | | |
| 5p | 7 | 6 | 2 | |
| 8q22-ter | 3 | 2 | 3 | 1 |
| 10p | 4 | 3 | | 1 |
| 11q13 | 7 | 6 | 4 | 2 |
| 12q21-24 | 5 | 4 | | |
| 15 | 8 | 6 | | |
| 16 | 12 | 10 | 1 | |
| 17p | 5 | 4 | | 1 |
| 17q | 11 | 9 | 2 | 1 |
| 18q | 10 | 8 | | 2 |
| 20q11-ter | 10 | 8 | 3 | 1 |
| 20 | 14 | 11 | 1 | 1 |

TABLE 10

Summary assessment of detected anomalies (deletions)

| BANDS | TOTAL CLONES | POSITIVE MINIMUM | Positive endo | Suspect positive endo (follow-up) |
|---|---|---|---|---|
| 2q35-ter | 2 | 2 | | |
| 4p | 3 | 2 | 1 | |
| 4q26-ter | 7 | 6 | | |
| 6q15-24 | 5 | 4 | 1 | |
| 6q25-27 | 5 | 4 | 1 | 1 |
| 8p | 14 | 11 | 2 | 2 |
| 9p | 6 | 5 | 3 | 1 |
| 9q | 12 | 10 | 1 | 1 |
| 10q | 14 | 11 | 1 | |
| 11p | 4 | 3 | 1 | 1 |
| 11q23-25 | 5 | 4 | 1 | |
| 13q13 | 3 | 2 | | |
| 13 | 7 | 6 | | |
| 14q23-31 | 3 | 2 | | |
| 17p | 5 | 4 | | |
| 17 | 16 | 13 | | |
| 18q12 | 3 | 2 | 2 | 1 |
| 18q12-23 | 11 | 9 | | 1 |
| 19 | 4 | 3 | | |

The results listed in Tables 9 and 10 show that many characteristic anomalies are detected in patients with positive endoscopy. However, suspect endoscopies reveal fewer alterations. In patients for whom the endoscopy diagnosis was not fully determined, the follow-up showed that these patients had progressed unfavorably. It thus seems that a suspect endoscopy would have been clarified by the inventors' test before reaching the 6-month follow-up.

It should also be noted that patients with negative endoscopy as well as those for whom the 12-month follow-up still revealed nothing, showed no positivity for the tested areas. (Only a few clones showed variations, but these were not areas intended to be tested, and corresponded to polymorphic variations of clones spotted on the slide. These clones will have to be suppressed in the forthcoming versions of the present slide, because of their varying nature and near-centromeric position.)

If the analysis is performed on a case by case basis on each of the DNAs extracted from the urine of a patient urine with positive endoscopy, the present invention's summary table, which combines a low grade or a high grade, may be applied.

Specific Examples

DNA 34016: UUTT with positive endoscopy. The 9p and 9q deletions, indicative of low grades, were detected. The inventors' urologist partner carried out a biopsy following the test. A grade 1 or 2 was determined.

DNA 33276: UUTT with positive endoscopy. Numerous anomalies (8 in total) are detected, among which 9q, 11p, 8p and 1q22-q2, which are characteristic of high grades. Following the biopsy, a grade G3 was confirmed.

DNA 32479: Bladder tumor with suspect endoscopy but positive follow-up at 6 months: a gain of 19 only was detected. This small number of anomalies and the undetermined influence of 19's gain, allow the inventors to associate this tumor with a low grade. The biopsy indicated grade G1/G2.

A biopsy was carried out on most of the patients whose urine was tested in this study, whenever their endoscopy was positive. At the time when the BCA test was carried out, the results of the biopsy were not available.

This test was thus carried out in the blind mode. Its results can be summarized for bladder cancer as shown in Table 11 below.

TABLE 11

Bladder tumor: positive endoscopy: 8 urine samples

| DNA # | POSITIVE MARKERS | BCA CONCLUSION | BIOPSY RESULT |
|---|---|---|---|
| Fb48 | None | Low Grade G1 | Non analyzable |
| 30869 | 8q22-qter, 11q13, 17q | Low Grade G2 | Non analyzable |
| 32479 | 19 | Low Grade G1 | G1/G2 |
| 32759 | 9p | Low Grade G1 | G1/G2 |
| Fb43 | 19 | Low Grade G1 | G1/G2 |
| 30656 | 6q25-q27 | Low Grade | Non analyzable |
| 32671 | 9p, 6q25-q27 | Low Grade progression | G3 |
| 31138 | None | Low Grade | Non analyzable |
| 33442 | 6q27, 8p, 17q | High Grade | G3 |
| 32924 | 5p, 8q, 11q13, 17q, 20, 8p, 9p, 9q, 10q, 11p, 16, 18q12, 22 | Very high grade | G3 |
| Fb13 | 6q25-q27, 9p, 14q22-qter, 11q13, 20, 22 | High Grade | G3 |
| 39373 | 5p, 8q22-qter, 18q12, 20 | High Grade | G3 |

It should be noted that for all patients for whom the result of the biopsy was unambiguous, it would have been possible to predict the grade of the tumor. Moreover, in some cases, a more accurate analysis of the altered markers provides information about the aggressive character of the tumor, its metastatic potential and its possible progression. Moreover, some biopsies that were too restricted could not be analyzed, whereas the present invention is able to provide a clear result concerning the grade of these tumors.

B—Oligonucleotide Microarray Preparation

Similar results as those presented above were obtained by using microarrays in which the reference DNAs are present in the form of oligonucleotide probes. The protocol carried out in this respect was as follows:

I—Determination of Integrity and Amount of Genomic DNA (gDNA)
 1. Measure gDNA concentration on Nanodrop ND-1000 spectrophotometer ($A_{260}/A_{280}$ ratio should be in range of 1.8-2.0, $A_{260}/A_{230}$ ratio should be >2.0),
 2. Confirm gDNA size by running ~200 ng of DNA on a 0.8-1% agarose gel (DNA should be of intact genomic size without any signs of degradation),
 3. Sonicate the samples,
 4. Aliquot 200 ng of sonicated test gDNA and 200 ng of sonicated reference gDNA into two separate 1.5 ml microcentrifuge tubes.

II—Fluorescent Labeling of Sonicated cDNA
 1. Thaw and add 12.2 ul Alexa Fluor® 2× Reaction Mixes (from the BioPrime Total Labeling Module) to the tubes containing sonicated gDNA
 2. Incubate samples (while protected from light) at 95° C. for 5 minutes.
 3. Immediately place the samples on ice (snap cool) for 5 minutes.
 4. Add 1.5 µl of Exo-Klenow Fragment (from the BioPrime Total Labeling Module) to each tube (50 ul total volume).
 5. Mix samples
 6. Incubate samples (while protected from the light) at 37° C. for 2 hours.

III—Purification of Labeled DNA
 1. Add 200 µl of Binding Buffer B2 (from the BioPrime Total Labeling Module) to each tube and vortex to mix.
 2. Load each sample containing B2 from Step 1 above onto a PureLink™ Spin Column (from the BioPrime Total Labeling Module), pre-inserted into a collection tube.
 3. Centrifuge at 10,000×g for 1 minute; discard the flow-through and place the column back in the collection tube.
 4. Add 650 µl of Wash Buffer W1 (from the BioPrime Total Labeling Module) to the column.
 5. Centrifuge at 10,000×g for 1 minute; discard the flow-through and place the column back in the collection tube.
 6. Spin at maximum speed for an additional 2-3 minutes to remove any residual wash buffer; discard the flow-through and the collection tube.
 7. Place the spin column in a new, sterile 1.5 ml microcentrifuge tube.
 8. Add 12.5 ul of water to the center of the column and incubate at room temperature for 1 minute.
 9. Centrifuge at maximum speed for 2 minutes; flow-through contains the purified labeled DNA probes (discard the column after use).
 10. Place 1.5 ul of each sample on the NanoDrop spectrophotometer to determine its yield and specific activity (use Microarray option).
 11. Combine test Alexa Fluor®-3 labeled sample with reference Alexa Fluor®-5 labeled sample.
 12. Aliquot 16.0 ul of combined mixture into a new 1.5 ml microcentrifuge tube.

IV—Preparation of Labeled gDNA for Hybridization
 1. Add components below in the order indicated in a nuclease-free tube:
    16.0 µl $AF_5$ and $AF_3$ labeled gDNA mixture;
    2.0 µl Cot-1 DNA (1 mg/ml)(prepared at 1000 ng/µl concentration);
    4.5 µl Agilent 10× Blocking Agent; and
    22.5 µl Agilent 2× Hybridization Buffer (q.s. 45 µl)
 2. Mix samples
 3. Incubate samples (while protecting from light) at 95° C. for 3 minutes.
 4. Immediately incubate tubes at 37° C. for 30 minutes.
 5. Spin tubes at maximum speed to collect the sample in the bottom of the tube.

V—Microarray Hybridization
 1. Load a clean 8×60K gasket slide into the Agilent SureHyb chamber base with the gasket label facing up and aligned with the rectangular section of the chamber base,
 2. Slowly dispense 45 ul of hybridization sample mixture into each gasket well in a drag and dispense manner.
 3. Place an 8×60K microarray slide ("active side" down) onto the gasket slide.
 4. Place the assembled slide chamber in the rotator rack in the rotating hybridization oven set to 65° C.
 5. Rotate at the samples at 20 rpm for 12-16 hours.

VI—Microarray Washing and Staining
1. Remove one hybridization chamber from incubator.
2. Disassemble the slide chamber.
3. Remove the microarray slide and place into slide rack in the slide staining dish #2 containing Oligo aCGH Wash Buffer 1 at room temperature. Minimize exposure of the slide to the air. Touch only barcode portion of the microarray slide or its edges.
4. When all slides are in the slide rack #2, stir (adjust the setting to get good but not vigorous mixing) for 5 minutes.
5. Transfer slide rack to slide staining dish #3 containing Oligo aCGH Wash Buffer 2 at 37° C., and stir (adjust the setting to get good but not vigorous mixing) for 1 minute.
6. Slowly remove slide rack trying to minimize droplets on the slides. It should take 5 to 10 seconds to remove the slide rack. If there are any remaining droplets on the array (DNA surface), spin the slide in the slide spinner for ~10 seconds.

The slides were scanned immediately, prior to computer image analysis.

The invention claimed is:

1. A DNA microarray for the detection of bladder cancer comprising, fixed on its surface, deposits of reference DNAs, said reference DNAs consisting of DNA sequences from each of the following loci of the human chromosomes: 3q, 8q22qter, 9p, 9q, 18q12, 1 q22-q24, 11q13, 13q, 7q, 8p, 11p, 14q22-qter, 17p and 22, wherein the DNA sequences are at least 30 bases in length.

2. The DNA microarray of claim 1, wherein the DNA sequences are 30 to 100 bases in length.

3. The DNA microarray of claim 1, wherein the DNA sequences are 1,000 to 200,000 bases in length.

4. The DNA microarray of claim 1, comprising 10 to 1000 reference DNA deposits.

5. The DNA microarray of claim 2, comprising between 1,000 and 60,000 reference DNA deposits.

6. The DNA microarray of claim 3, comprising between 300 to 400 DNA deposits.

7. A method for analyzing a urine sample taken from a patient, comprising:
(i) extracting DNA contained in said urine sample taken from said patient;
(ii) fragmenting the DNA extracted in step (i);
(iii) marking the obtained DNA fragments uniformly with a marking agent so as to form a pool of marked DNA;
(iv) forming at least one aliquot from the pool of marked DNA and bringing each aliquot into contact with a set of reference DNAs, said contact being carried out under conditions enabling specific hybridization of the marked DNA fragments with said reference DNAs; said reference DNAs comprising DNA sequences from the following loci present in the human chromosomes: 3q, 8q22qter, 9p, 9q, 18q12, 1 q22-q24, 11q13, 13q, 7q, 8p, 11p, 14q22-qter, 17p and 22, wherein the reference DNAs are at least 30 bases in length;
(v) eliminating the marked DNA fragments which are not specifically hybridized to the reference DNAs; and
(vi) determining the intensity of the signal produced by the marked fragments hybridized to each of the selected reference DNAs.

8. The method according to claim 7, wherein the DNA fragments taken from the patient in step (iii) are divided into two pools, one being marked with a first marker and the second with a second marker, the control DNA of step (vii) being also divided into two pools, one being marked with the first marker and the second with the second marker, a cross-determination of the signal deviation being carried out in step (vii) between each of the thus marked pools.

9. The method according to claim 7, wherein the reference DNAs are deposited separately on a microarray, prior to hybridization with the marked DNA fragments.

10. The method according to claim 7, wherein the DNA sequences are probes of 30 to 100 bases.

11. The method according to claim 7, wherein the DNA sequences are 1,000 to 200,000 bases in length.

12. The method according to claim 7, comprising 10 to 1000 reference DNA deposits.

13. The method according to claim 7, comprising between 1,000 and 60,000 reference DNA deposits.

14. The method according to claim 7, wherein the reference DNAs in steps (iv) and (viii), additionally comprise DNA sequences of at least 30 bases in length included in each of the following additional loci of the human chromosomes: 1p, 20, 5p12-p13, 5p, 6q22, 7, 12q15, 15, 16, 17q, 6q25-q27, 10q, and 19.

15. The method according to claim 14, wherein the DNA fragments taken from the patient in step (iii) are divided into two pools, one being marked with a first marker and the second with a second marker, the control DNA of step (vii) being also divided into two pools, one being marked with the first marker and the second with the second marker, a cross-determination of the signal deviation being carried out in step (vii) between each of the thus marked pools.

16. The method according to claim 14, wherein the reference DNAs are deposited separately on a microarray, prior to hybridization with the marked DNA fragments.

17. The method according to claim 14, wherein the DNA sequences are probes of 30 to 100 bases.

* * * * *